(12) United States Patent
Parsonson

(10) Patent No.: US 9,186,363 B1
(45) Date of Patent: Nov. 17, 2015

(54) PHARMACEUTICAL COMPOSITION AND METHOD FOR TREATING AGE-RELATED MACULAR DEGENERATION

(71) Applicant: Peter Shepherd Parsonson, Dallas, TX (US)

(72) Inventor: Peter Shepherd Parsonson, Dallas, TX (US)

( * ) Notice: Subject to any disclaimer, the term of this patent is extended or adjusted under 35 U.S.C. 154(b) by 0 days.

(21) Appl. No.: 14/587,604

(22) Filed: Dec. 31, 2014

(51) Int. Cl.
*A61K 31/541* (2006.01)
*A61K 36/282* (2006.01)

(52) U.S. Cl.
CPC .............. *A61K 31/541* (2013.01); *A61K 36/282* (2013.01)

(58) Field of Classification Search
CPC .................................................... A61K 31/541
USPC ....................................................... 514/228.5
See application file for complete search history.

(56) References Cited

PUBLICATIONS

Waknine-Grinberg et al., Malaria J. (2010), 9:227, pp. 1-15.*

* cited by examiner

*Primary Examiner* — Taofiq A Solola

(57) ABSTRACT

The present invention teaches a new and innovative pharmaceutical composition and method for the treatment of age-related macular degeneration in a patient in need thereof. In particular, the present invention teaches the administration of artemisone for the treatment and/or prevention of AMD in a patient in need thereof. This invention relates to one certain extract of the Artemisia annua plant, both in its crude and refined form composed substantially of Artemisone, a compound that is chemically classified as a sesquiterpene with an endo-peroxide group [FIG. 1]. The present invention teaches a for the treatment of either wet or dry age-related macular degeneration. The invention provides for an initial treatment using an intravitreal injection of Artemisone followed by the use of an oral dosage form which is designed to maintain the therapeutic concentration of Artemisone in the eye without having to perform constant intravitreal injections into the eye.

13 Claims, 1 Drawing Sheet

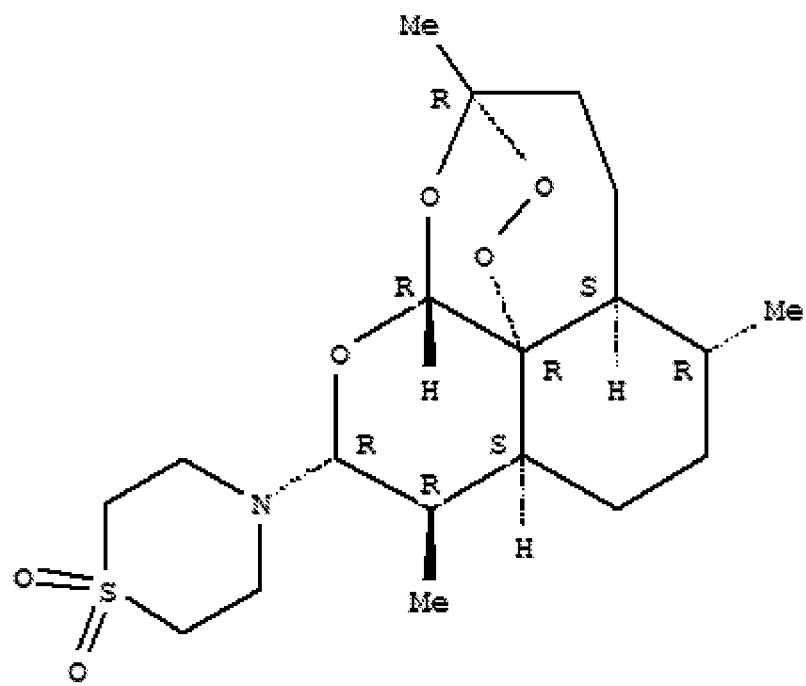
Chemical Structure of Artemisone

PHARMACEUTICAL COMPOSITION AND METHOD FOR TREATING AGE-RELATED MACULAR DEGENERATION

BRIEF SUMMARY OF THE INVENTION

The present invention teaches a new and innovative pharmaceutical composition and method for the treatment of age-related macular degeneration in a patient in need thereof. In particular, the present invention teaches the administration of artemisone for the treatment and/or prevention of AMD in a patient in need thereof. More specifically, patients identified as having AMD or at high risk for developing AMD can be treated with therapeutic and/or prophylactic amounts of artemison for preventing or inhibiting the progression of the disease.

Thus the present invention teaches specific formulations of artemisone pharmaceutical compositions suitable for administration to a patient in need of treatment for AMD, for the prophylactic treatment against AMD, or for the therapeutic and/or prophylactic prevention of advancement of AMD disease in a patient in need thereof.

The present invention teaches a method for treating and/or preventing age-related macular degeneration in a patient identified as in need thereof, said method comprising identifying a patient in need of treatment for age-related macular degeneration, and administering a therapeutic amount of artemisone to said patient.

The present invention teaches a method as above, wherein the patient is identified via visual examination of the patient's eye.

The present invention teaches a method as above, wherein the patient is identified via screening according to risk-factor criteria.

The present invention teaches a method as above, wherein said age-related macular degeneration is the dry form.

The present invention teaches a method as above, wherein said age-related macular degeneration is the wet form.

The present invention teaches a method as above, wherein said age-related macular degeneration occurs in one eye.

The present invention teaches a method as above, wherein said age-related macular degeneration occurs in two eyes.

The present invention teaches a method as above, wherein said administration of artemisone is via an oral dosage form.

The present invention teaches a method as above, wherein said administration of artemisone is via an injectible dosage form such as intravitreal administration.

The present invention teaches wherein said administration of artemisone is via a liquid, powder, ointment, paste, gel or cream dosage form.

The present invention teaches wherein said artemisone is administered in a dose of from 0.1 mg to 500 mg.

The present invention teaches wherein said artemisone is administered once via an injection preferably intravitreal administration. Treatment is then followed up with oral administration to maintain the artemisone levels in the eye.

The present invention teaches wherein said artemisone is administered in a dose once daily.

The present invention teaches wherein said artemisone is administered in the evening.

The present invention teaches wherein said artemisone is administered prior to sleep.

The present invention also teaches wherein said artemisone is administered in a dose twice daily.

The present invention teaches wherein said artemisone is administered in a dose more than twice daily.

The present invention further teaches a pharmaceutical composition comprising a therapeutic amount of artemisone and a pharmaceutically acceptable carrier, excipient or diluent.

BRIEF DESCRIPTION OF THE DRAWINGS

FIG. 1. shows the chemical structure of Artemisone and its endoperoxide bridge.

DETAILED DESCRIPTION AND BEST MODE OF IMPLEMENTATION

This invention relates to certain extracts of the *Artemisia* annua plant, both in their crude and refined forms, and certain refined forms of *Artemisia* annua plant extracts composed specifically of Artemisone FIG. 1, which is chemically classified as a sesquiterpene containing an endo-peroxide bridge. The compound is suitable for oral administration as well as intravitreal or injection administration.

The present invention discloses a method of intravitreal, topical, parenteral, or oral administration of Artemisone as a refined form from the *Artemisia* annua plant composed substantially of Artemisone. This method can include a base, a carrier, a solvent or a delivery system.

*Artemisia* annua extracts have been used in ancient Chinese medicine (qinqhao) for a number of treatments. Medicinal use of the Chinese herb qinqhao appears in several standard Chinese Materia Medica texts as a treatment for febrile illnesses. The herb was specifically recommended for fevers in the Zhou Hou Bei fi Fang (The Handbook of Prescriptions for Emergencies) written by Ge Heng and published in 341 AD. The most detailed description appears in the "Compendium of Materia Medica- Ben Cao Gang Mu, compiled in 1596, and is still printed in China today. The antimalarial activity of qinqhao was rediscovered in China in 1972, and the antimalarial active principal of qinqhao was named "qinghaosu". The western name for the compound is artemisinin. Recently, however, this extract and its sesquiterpene derivatives have been used for the treatment of malaria. Distribution of artemisinin in *Artemisia* annua has been reviewed [Ferreira et al., Progress in New Crops, J. Janick (ed.), ASHS Press 579 (1996)].

Moreover, it has been disclosed that Artemisone FIG. 1 is a highly potent and active agent in delivering the antimalarial benefits of *Artemisia* annua extracts. Only orally administered compositions seem to provide antimalarial benefits.

Artemisinin (Qinghaosu) and its analogs including Artemisone are the treatments of choice for cerebral or chloroquine resistant malaria or for patients with chloroquine allergy. Artemisone is a sesquiterpene lactone with a peroxide bridge, and is characterized by very low toxicity. Artemisone stimulates cell-mediated immunity, and yet decreases abnormally elevated levels of polyamine regulatory proteins. It also markedly inhibits nucleic acid and protein syntheses. Further, it affects cellular membrane functions and decreases hepatic cytochrome oxidase enzyme system activity. Still further, it is virustatic against influenza and cidal against three groups of pathogenic parasites.

The very low toxicity of this compound to humans is a major benefit. For example, artesunate is twice as safe as artemether and only one-fiftieth as toxic as chloroquinine, the most common antimalarial. The first manifestation of toxicity of these compounds is generally a decreased reticulocyte count. Other manifestations include transient fever, decreased appetite and elevated blood transaminase levels, the latter an indication of hepatotoxicity.

In the present invention it is thus both surprising and unexpected that Artemisone can be utilized in intravitreal, and topical or orally administered formulations as a treatment for age related macular degeneration.

Age-related macular degeneration (AMD) means the pathological condition of the retina which is characterized by physical changes in the macular region of the retina and presents with loss of central vision in the patient.

AMD can be diagnosed by physical direct or indirect examination of the retina to detect and/or identify characteristic physical appearances of the macular region of the retina which are not considered normal. In particular, the identification of drusen deposits containing amyloid in the case of dry AMD, or abnormal blood vessel formations in the case of wet AMD. Patients with a propensity for AMD or an increased risk for AMD can be identified via selection criteria scored according to risk factors. The selection criteria include physical factors such as age of patient (the older, the greater the risk); family history (if yes, then greater risk), and occupational or environmental factors such as exposure to bright sunlight (the greater the exposure, the greater the risk); exposure to bright lights (the greater the exposure, the greater the risk).

Artemisone has low toxicity and can be administered safely through oral or parenteral routes (e.g., for local administration, rectal administration, intravenous administration, intravitreal administration etc.), either directly or as pharmaceutical compositions to be mixed with pharmaceutically acceptable carriers by using known methods, for example, as tablets (including sugar-coated tablets, film-coated tablets), powders, granules, capsules (including soft capsules), liquids, eye drops, injections, suppositories, sustained release preparations, plasters and also as chewing gum, etc. Administration may be oral, by inhalation, topical, transmucosal, parenteral, intravenous or intraocular.

Pharmacologically acceptable carriers that may be used to produce the phamiaceutical compositions of the present invention include various organic or inorganic carrier substances in common use as pharmaceutical materials, including excipients, lubricants, binders, disintegrants, water-soluble polymers and basic inorganic salts for solid preparations; and solvents, dissolution aids, suspending agents, isotonizing agents, buffers and soothing agents for liquid preparations. Other ordinary pharmaceutical additives such as preservatives, antioxidants, coloring agents, sweetening agents, souring agents, bubbling agents and flavorings may also be used as necessary.

Such "excipients" include, for example, lactose, sucrose, D-mannitol, starch, cornstarch, crystalline cellulose, light silicic anhydride and titanium oxide.

Such "lubricants" include, for example, magnesium stearate, sucrose fatty acid esters, polyethylene glycol, talc and stearic acid.

Such "binders" include, for example, hydroxypropyl cellulose, hydroxypropylmethyl cellulose, crystalline cellulose, polyvinylpyrrolidone, gum arabic powder, gelatin, pullulan and low-substitutional hydroxypropyl cellulose.

Such "disintegrants" include (1) crosslinked povidone, (2) super-disintegrants such as crosslinked carmellose sodium (FMC-Asahi Chemical) and carmellose calcium (Gotoku Yakuhin), (3) carboxymethyl starch sodium (e.g., product of Matsutani Chemical), (4) low-substituted hydroxypropyl cellulose (e.g., product of Shin-Etsu Chemical), (5) cornstarch, and so forth. Said "crosslinked povidone" may be any crosslinked polymer having the chemical name 1-ethenyl-2-pyrrolidinone homopolymer, including polyvinylpyrrolidone (PVPP) and 1-vinyl-2-pyrrolidinone homopolymer, and is exemplified by Colidon CL (produced by BASF), Polyplasdon XL (produced by ISP), Polyplasdon XL-10 (produced by ISP) and Polyplasdon INF-10 (produced by ISP).

Such "water-soluble polymers" include, for example, ethanol-soluble water-soluble polymers [e.g. cellulose derivatives such as hydroxypropyl cellulose (hereinafter also referred to as HPC), polyvinylpyrrolidone] and ethanol-insoluble water-soluble polymers [e.g., cellulose derivatives such as hydroxypropylmethyl cellulose (hereinafter also referred to as HPMC), methyl cellulose and carboxymethyl cellulose sodium, sodium polyacrylate, polyvinyl alcohol, sodium alginate, guar gum].

Such "basic inorganic salts" include, for example, basic inorganic salts of sodium, potassium, magnesium and/or calcium. Preferred are basic inorganic salts of magnesium and/or calcium. More preferred are basic inorganic salts of magnesium. Such basic inorganic salts of sodium include, for example, sodium carbonate, sodium hydrogen carbonate, disodium hydrogenphosphate, etc. Such basic inorganic salts of potassium include, for example, potassium carbonate, potassium hydrogen carbonate, etc. Such basic inorganic salts of magnesium include, for example, heavy magnesium carbonate, magnesium carbonate, magnesium oxide, magnesium hydroxide, magnesium metasilicate aluminate, magnesium silicate, magnesium aluminate, synthetic hydrotalcite [$Mg_6Al_2(OH)_{16}CO_3\cdot 4H_2O$] and so forth. Among others, preferred is heavy magnesium carbonate, magnesium carbonate, magnesium oxide, magnesium hydroxide, etc. Such basic inorganic salts of calcium include, for example, precipitated calcium carbonate, calcium hydroxide, etc.

Such "solvents" include, for example, water for injection, alcohol, propylene glycol, macrogol, sesame oil, corn oil and olive oil.

Such "dissolution aids" include, for example, polyethylene glycol, propylene glycol, D-mannitol, benzyl benzoate, ethanol, trisaminomethane, cholesterol, triethanolamine, sodium carbonate and sodium citrate.

Such "suspending agents" include, for example, surfactants such as stearyltriethanolamine, sodium lauryl sulfate, laurylaminopropionic acid, lecithin, henzalkonium chloride, henzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose.

Such "isotonizing agents" include, for example, glucose, D-sorbitol, sodium chloride, glycerol and D-mannitol.

Such "buffers" include, for example, buffer solutions of phosphates, acetates, carbonates, citrates etc.

Such "soothing agents" include, for example, benzyl alcohol.

Such "preservatives" include, for example, p-oxybenzoic acid esters, chlorobutanol, benzyl alcohol, phenethyl alcohol, dehydroacetic acid and sorbic acid.

Such "antioxidants" include, for example, sulfites, ascorbic acid and alpha D-tocopherol.

Such "coloring agents" include, for example, food colors such as Food Color Yellow No. 5, Food Color Red No. 2 and Food Color Blue No. 2; and food lake colors and red oxide.

Such "sweetening agents" include, for example, saccharin sodium, dipotassium glycyrrhetinate, aspartame, stevia and thaumatin.

Such "souring agents" include, for example, citric acid (citric anhydride), tartaric acid and malic acid.

Such "bubbling agents" include, for example, sodium bicarbonate.

Such "flavorings" may be synthetic substances or naturally occurring substances, and include, for example, lemon, lime, orange, menthol and strawberry.

The content of artemisone is usually about 0.01 to 100% by weight based on a total weight of the composition.

Additionally, artemisone can also be used in combination with other drugs such as H1 antagonists, anti-VEGF antibodies, anti-VEGF aptamer, VEGF receptor protein kinase inhibitor, synthetic steroid, vitamin A, vitamin C, vitamin E, .beta. carotene, lutein and zinc. An example of an aptamer is pegaptanib sodium. Examples of antibodies include bevacizumab and ranibizumab.

The composition comprises the other drugs are prepared by using known methods, for example, as tablets (including sugar-coated tablets, film-coated tablets), powders, granules, capsules (including soft capsules), liquids, injections, suppositories, sustained release preparations, plasters and also as chewing gum, etc. The compound may be administered as an immediate release form, a controlled release form or a sustained release form.

I claim:

1. A method for treating age-related macular degeneration in a patient in need thereof, wherein said method comprises identifying a patient in need of treatment for age-related macular degeneration, and administering Artemisone to said patient.

2. The method of claim 1, wherein the patient is identified by visual examination of the patient.

3. The method of claim 1, wherein said age-related macular degeneration is the dry form.

4. The method of claim 1, wherein said age-related macular degeneration is the wet form.

5. The method of claim 1, wherein said age-related macular degeneration occurs in one eye.

6. The method of claim 1, wherein said age-related macular degeneration occurs in two eyes.

7. The method of claim 1, wherein said administration of Artemisone is by an oral dosage form.

8. The method of claim 1, wherein said administration of Artemisone is by an injectable dosage form.

9. The method of claim 1, wherein said Artemisone is administered in an oral doseage form of from 1 mg to 1000 mg.

10. The method of claim 8, wherein said Artemisone, is administered in an injectable dosage form of from 0.1 mg to 500 mg.

11. The method of claim 1, wherein said Artemisone is administered orally in a dose once weekly.

12. The method of claim 8, wherein said Artemisone is administered intravitreally in a dose once every three months.

13. The method of claim 8, wherein said Artemisone is administered intravitreally in a dose once every six months.

\* \* \* \* \*